(12) United States Patent
Yagi et al.

(10) Patent No.: US 7,514,663 B2
(45) Date of Patent: Apr. 7, 2009

(54) IMAGING APPARATUS HAVING A READ OUT CIRCUIT UNIT WITH DUAL READOUT OPERATION AND METHOD OF IMPROVING A FRAME RATE

(75) Inventors: Tomoyuki Yagi, Honjo (JP); Tadao Endo, Honjo (JP); Toshio Kameshima, Kumagaya (JP); Katsuro Takenaka, Honjo (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 22 days.

(21) Appl. No.: 11/765,107

(22) Filed: Jun. 19, 2007

(65) Prior Publication Data

US 2008/0029688 A1 Feb. 7, 2008

(30) Foreign Application Priority Data

Aug. 4, 2006 (JP) ............................. 2006-213470

(51) Int. Cl.
*H01L 27/00* (2006.01)
(52) U.S. Cl. ................................. 250/208.1; 250/214 R
(58) Field of Classification Search .............. 250/208.1, 250/214 R, 370.09, 370.11; 600/160, 168, 600/410, 419, 423, 432, 443, 463; 128/925; 348/311–319, 294–303
See application file for complete search history.

(56) References Cited

U.S. PATENT DOCUMENTS 5,014,711 A * 5/1991 Nagasaki ..................... 600/443

| | | | |
|---|---|---|---|
| 6,952,015 B2 | 10/2005 | Kameshima | 250/370.11 |
| 6,952,464 B2 | 10/2005 | Endo | 378/98.11 |
| 6,985,555 B2 | 1/2006 | Endo | 378/98.11 |
| 7,002,157 B2 | 2/2006 | Kameshima | 250/370.11 |
| 7,012,260 B2 | 3/2006 | Endo | 250/370.11 |
| 7,022,997 B2 | 4/2006 | Kaifu et al. | 250/370.14 |
| 7,138,639 B2 | 11/2006 | Kameshima | 250/370.11 |
| 7,154,099 B2 | 12/2006 | Endo | 250/370.11 |
| 7,227,926 B2 | 6/2007 | Kameshima et al. | 378/98.9 |
| 2005/0109927 A1 | 5/2005 | Takenaka et al. | 250/370.09 |

(Continued)

FOREIGN PATENT DOCUMENTS

JP 7-322141 12/1995

*Primary Examiner*—Que T Le
(74) *Attorney, Agent, or Firm*—Fitzpatrick, Cella, Harper & Scinto

(57) ABSTRACT

An image apparatus capable of improving a frame rate to prevent resolution in the predetermined area from decreasing and forming image signals outside the predetermined area has an area sensor in which a plurality of pixels is arranged in a matrix, a drive circuit unit, a read out circuit unit and a processing unit processing signals transferred from the read out circuit unit. The drive circuit unit and the read out circuit unit perform a first operation in which signals are simultaneously read out from N pixels in a first area of the area sensor (where N is an integer equal to one or more) and a second operation in which signals are simultaneously read out from M pixels in a second area except the first area of the area sensor (where M is an integer equal to two or more and always greater than N), the first and second read out operations are continuously performed in one frame period, and a first and a second signal obtained by the first and the second read out operations are continuously transferred from the read out circuit unit to the processing unit.

11 Claims, 12 Drawing Sheets

U.S. PATENT DOCUMENTS

| | | |
|---|---|---|
| 2005/0199834 A1 | 9/2005 | Takenaka et al. ............. 250/580 |
| 2005/0200720 A1 | 9/2005 | Kameshima et al. ..... 348/220.1 |
| 2005/0220269 A1 | 10/2005 | Endo et al. ................. 378/114 |
| 2005/0264665 A1 | 12/2005 | Endo et al. ................. 348/308 |
| 2006/0119719 A1 | 6/2006 | Kameshima ................ 348/308 |
| 2006/0192130 A1 | 8/2006 | Yagi ...................... 250/370.14 |
| 2006/0289774 A1 | 12/2006 | Endo et al. ............ 250/370.09 |
| 2007/0040099 A1 | 2/2007 | Yokoyama et al. ....... 250/208.1 |
| 2007/0069144 A1 | 3/2007 | Kameshima ........... 250/370.09 |
| 2007/0080299 A1 | 4/2007 | Endo et al. ............ 250/370.09 |
| 2007/0096032 A1 | 5/2007 | Yagi et al. .............. 250/370.11 |
| 2007/0125952 A1 | 6/2007 | Endo et al. .................. 250/369 |
| 2007/0131843 A1 | 6/2007 | Yokoyama et al. .......... 250/205 |
| 2007/0183573 A1 | 8/2007 | Kameshima et al. ....... 378/98.9 |
| 2007/0210258 A1 | 9/2007 | Endo et al. ............ 250/370.09 |
| 2007/0290143 A1 | 12/2007 | Kameshima et al. ... 250/370.09 |
| 2007/0291904 A1 | 12/2007 | Takenaka et al. ............ 378/207 |
| 2007/0297567 A1 | 12/2007 | Takenaka et al. ........... 378/98.2 |
| 2008/0011958 A1 | 1/2008 | Endo et al. ............ 250/370.08 |
| 2008/0013686 A1 | 1/2008 | Kameshima et al. .......... 378/98 |
| 2008/0054182 A1 | 3/2008 | Yokoyama et al. ..... 250/370.09 |

\* cited by examiner

IMAGING APPARATUS HAVING A READ OUT CIRCUIT UNIT WITH DUAL READOUT OPERATION AND METHOD OF IMPROVING A FRAME RATE

BACKGROUND OF THE INVENTION

1. Field of the Invention

The present invention relates to an imaging apparatus, a radiation imaging apparatus and a radiation imaging system, and more specifically, to an imaging apparatus used in a radiation imaging apparatus and radiation imaging system suitably used for still image radiographing such as plain radiographing and moving image radiographing such as fluoroscopy in medical diagnosis and an imaging apparatus used in a radiation imaging system. In the present invention, radiation includes not only alpha rays, beta rays and gamma rays being beams produced by particles (including photons) emitted by radioactive decay, but beams whose energy are nearly equal to or greater than the above, such as, for example, X rays, corpuscular rays and cosmic rays.

2. Description of the Related Art

In recent years, a radiation imaging apparatus using a flat panel detector (hereinafter, referred to as FPD) formed by a thin film semiconductor material over an insulating substrate has been practically applied as an imaging apparatus used for medical image diagnosis and non-destructive inspection using X rays. The radiation imaging apparatus using the FPD enables a digital radiographing in which radiation such X rays transmitted through an object such as a patient is converted into an analog electric signal by the FPD and the analog electric signal is then converted into a digital image signal. The FPD is roughly classified into two types: direct conversion and indirect conversion. The direct conversion type of a radiation imaging apparatus has an FPD including a two-dimensional area sensor in which a plurality of pixels are two-dimensionally arranged which include conversion elements using semiconductors such as a-Se capable of directly converting radiation into electric charge. The indirect conversion type of a radiation imaging apparatus has an FPD including a two-dimensional area sensor in which a plurality of pixels are two-dimensionally arranged which include a wavelength converter such as phosphor capable of converting radiation into light and a photoelectric conversion element using semiconductors such as a-Si capable of converting light into electric charge. The indirect conversion type of a radiation imaging apparatus is disclosed in U.S. Pat. No. 7,022,997, for example. The radiation imaging apparatus with the FPD is capable of replacing radiation image with digital information, enabling image information to be momentarily transmitted over distance. The radiation imaging apparatus with the FPD is used as a digital imaging apparatus for still image radiographing such as plain radiographing and moving image radiographing such as fluoroscopy in medical image diagnosis, for example.

One method is based on pixel addition. The following describes pixel addition. In general, the two-dimensional area sensor sequentially reads signals from pixels on a row and/or a column basis. However, the more the number of pixels in the two-dimensional area sensor, the longer the time (or one frame time) required to sequentially read out signals from pixels for one frame on a row basis and/or on a column basis. For this reason, a method referred to as "pixel addition" is used as described in Japanese Patent Application Laid-Open No. H07-322141 in which signals are simultaneously read from a plurality of pixels on a plural row basis and/or on a plural column basis to accelerate a scanning speed to shorten one frame time, improving a frame rate. The pixel addition method enables the frame rate to be improved and sensitivity to be improved because the method treats a signal from a plurality of pixels as one synthesized pixel.

Another method is based on trimming. The following describes trimming. Trimming is a method of selectively reading out signals from pixels in a predetermined area. Only signals from arbitrary pixels are sequentially read out on a row basis and/or on a column basis, and signals from other pixels are not read out or signals from other pixels are simultaneously read out. U.S. Pat. No. 6,690,493 discloses the trimming.

However, the pixel addition is lower in resolution than the method in which signals are sequential read out. For this reason, it may be difficult for the pixel addition to adapt to a part such as a heart that moves quickly and has minute vessels.

In the trimming, signals from the pixels outside a predetermined area are not read out or those are simultaneously read out, so that image signals cannot be formed from signals from the pixels outside the predetermined area. Accordingly, when the trimming is used for monitoring when a catheter is inserted or surgical operation is conducted in fluoroscopy, images outside the predetermined area cannot be formed, so that it may be difficult to follow an object moved outside the predetermined area.

SUMMARY OF THE INVENTION

The present invention has been made in view of the above problems and has for its purpose to provide an image apparatus capable of improving a frame rate to prevent resolution in the predetermined area from decreasing and forming image signals outside the predetermined area.

The image apparatus according to the present invention is characterized by including an area sensor in which a plurality of pixels is arranged in a matrix, the pixels including conversion elements for converting incident radiation or light into electric charge; a drive circuit unit for supplying a drive signal to a plurality of drive wirings arranged in a column direction, wherein the drive wiring is connected commonly to a plurality of pixels arranged in a row direction; a read out circuit unit for reading out signals from the pixels through a plurality of signal wirings arranged in the row direction, wherein the signal wiring is connected commonly to the plurality of pixels arranged in the column direction; and a processing unit processing signals transferred from the read out circuit unit; wherein N is an integer of one or more, M is an integer of two or more and always greater than N, the drive circuit unit and the read out circuit unit perform a first operation in which signals are simultaneously read out from N pixels in a first area of the area sensor and a second operation in which signals are simultaneously read out from M pixels in a second area except the first area of the area sensor, the first and the second read out operation are continuously performed in a period while signals are read out from all pixels of the area sensor, and a first signal obtained by the first read out operation and a second signal obtained by the second read out operation are continuously transferred from the read out circuit unit to the processing unit.

In a method of driving an imaging apparatus according to the present invention, the imaging apparatus including an area sensor in which a plurality of pixels is arranged in a matrix, the pixels including conversion elements for converting incident radiation or light into electric charge; a drive circuit unit for supplying a drive signal to a plurality of drive wirings arranged in a column direction, wherein the drive wiring is connected commonly to a plurality of pixels arranged in a row direction; a read out circuit unit for reading out signals from the pixels through a plurality of signal wirings arranged in the row direction, wherein the signal wiring is connected commonly to the plurality of pixels arranged in the column direction; and a processing unit processing signals transferred from the read out circuit unit; wherein N is an integer of one or more, M is an integer of two or more and always greater than N, the drive circuit unit and the read out circuit unit perform a first operation in which signals are simultaneously read out from N pixels in a first area of the area sensor and a second operation in which signals are simultaneously read out from M pixels in a second area except the first area of the area sensor, the first and the second read out operations are continuously performed in a period while signals are read out from all pixels of the area sensor, and a first signal obtained by the first read out operation and a second signal obtained by the second read out operation are continuously transferred from the read out circuit unit to the processing unit.

According to the present invention, image signals are read out with a scanning time shortened outside the predetermined area which is not required for surgical operation and diagnosis and only a target portion (or the predetermined area) being a portion required for surgical operation and diagnosis is scanned, so that a required resolution can be obtained in the predetermined area without scarifying the frame rate.

According to the present invention, a single radiation imaging apparatus can adapt to wider imaging means from fluoroscopy of small parts to plain radiographing of chest, improving the workflow of operation and lightening a burden to a patient.

Further features of the present invention will become apparent from the following description of exemplary embodiments with reference to the attached drawings.

DESCRIPTION OF THE EMBODIMENTS

Exemplary embodiments for carrying out the present invention are described below with reference to the drawings. Incidentally, although X rays are used as radiation in the embodiment of the present invention, the radiation of the present invention is not limited to X rays, but includes electromagnetic waves such as alpha rays, beta rays and gamma rays.

First Embodiment

Figure 1:
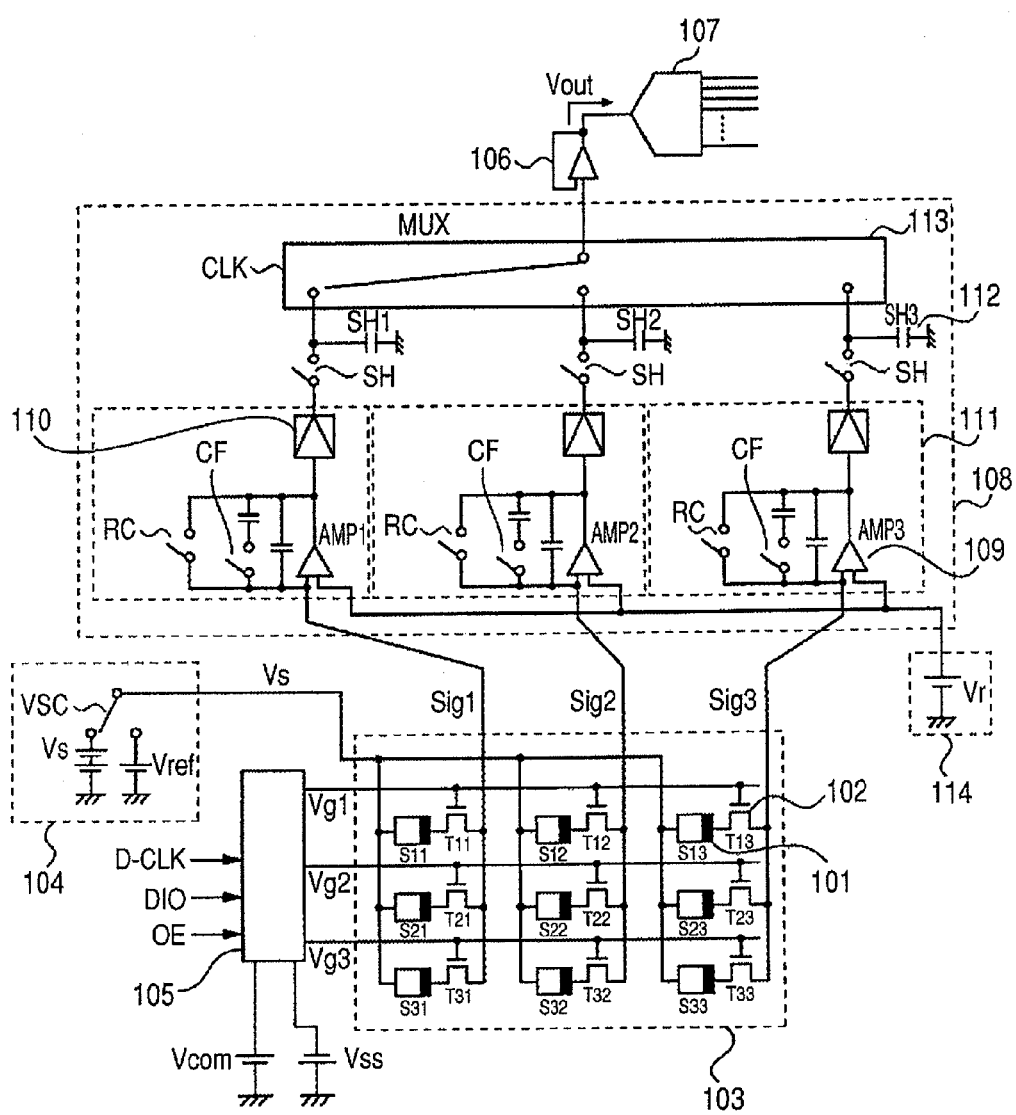
FIG. 1 is a schematic circuit diagram of an FPD used in a radiation imaging apparatus according to the present invention.

FIG. 1 is a schematic circuit diagram of an FPD used in the radiation imaging apparatus according to the present invention. In FIG. 1, the FPD includes a photoelectric conversion element 101 forming conversion elements for converting radiation into electric charge and a thin film transistor (TFT) 102 being a switching element for transferring an electric signal based on electric charge converted by the photoelectric conversion element 101. One pixel includes at least a pair of the photoelectric conversion element 101 and the TFT 102. The FPD further includes a two-dimensional area sensor 103 in which a plurality of pixels are two-dimensionally arranged in the row and the column direction. A bias power supply 104 supplies a bias required for photoelectric conversion to the photoelectric conversion element 101 and is connected to one of the electrodes of the photoelectric conversion element 101 through a bias wiring Vs. A drive circuit 105 controls the conduction state of TFTs 102 to drive them to scan the two-dimensional area sensor 103 and supplies drive signals to the TFTs 102 through drive wirings Vg1 to Bg3 commonly connected to the control electrodes of a plurality of the TFTs 102 on a row basis. A read out circuit 108 reads out an electric signal from the two-dimensional area sensor 103 and is connected to each pixel through signal wirings Sig 1 to Sig 3 commonly connected to a plurality of the TFTs 102 on a column basis. The read out circuit 108 includes an amplifier unit 111, sampling and holding circuit 112 and analog multiplexer 113. The amplifier unit 111 includes an amplifier 109 connected to each of the signal wirings Sig 1 to Sig 3 and a variable gain amplifier 110 arranged at the rear stage of the amplifier 109 and amplifies an electric signal from the two-dimensional area sensor 103. The sampling and holding circuit 112 serves to temporarily hold an electric signal amplified by each amplifier 109 and is connected to each amplifier 109. An analog multiplexer 113 serves to convert an electric signal read out in parallel and held in each sampling and holding circuit 112 into series signal to be read out as image signal for one row and is connected to each sampling and holding circuit 112 to sequentially select it. A buffer amplifier 106 receives a series-converted image signal for one row and performs impedance conversion. An analog-to-digital converter 107 (hereinafter, referred to as "A/D converter") converts an image signal being an analog signal transferred from the read out circuit 108 into image data being a digital signal. The FPD further includes a reference power supply 114 for the amplifier 109.

The drive circuit 105 is formed with a shift register. Control signals D-CLK, OE and DIO repeat ON/OFF operation of the drive wirings Vg1 to VG3. The control signal D-CLK is a shift clock of the shift register. The control signal DIO is a pulse transferred from the shift register. The control signal OE controls the output terminal of the shift register. A gate pulse (drive signal) formed of voltage Vcom for turning ON (conduction) the TFT 102 and voltage Vss for turning OFF (non-conduction) the TFT 102 is determined by the output of the shift register and the control signal OE. When the control signal OE is in a Low state, the voltage Vss is output to the drive wiring irrespective of whether the shift register is in a High or Low state. Only when the shift register is in a High state and the control signal OE is in a High state of Hi, the voltage Vcom is output to the drive wiring to turn on the TFT. The control signal D-CLK supplied to the drive circuit 105 is different among the drive circuits. This is because the number of pixels to be added is changed for each drive circuit. For this reason, the number of pixels to be added needs to be minutely switched in one image, the number of drive wirings allocated per drive circuit may be reduced to increase the number of the drive circuits. The control signals D-CLK, OE and DIO are supplied to the drive circuit by a control circuit (not shown).

Figure 2:
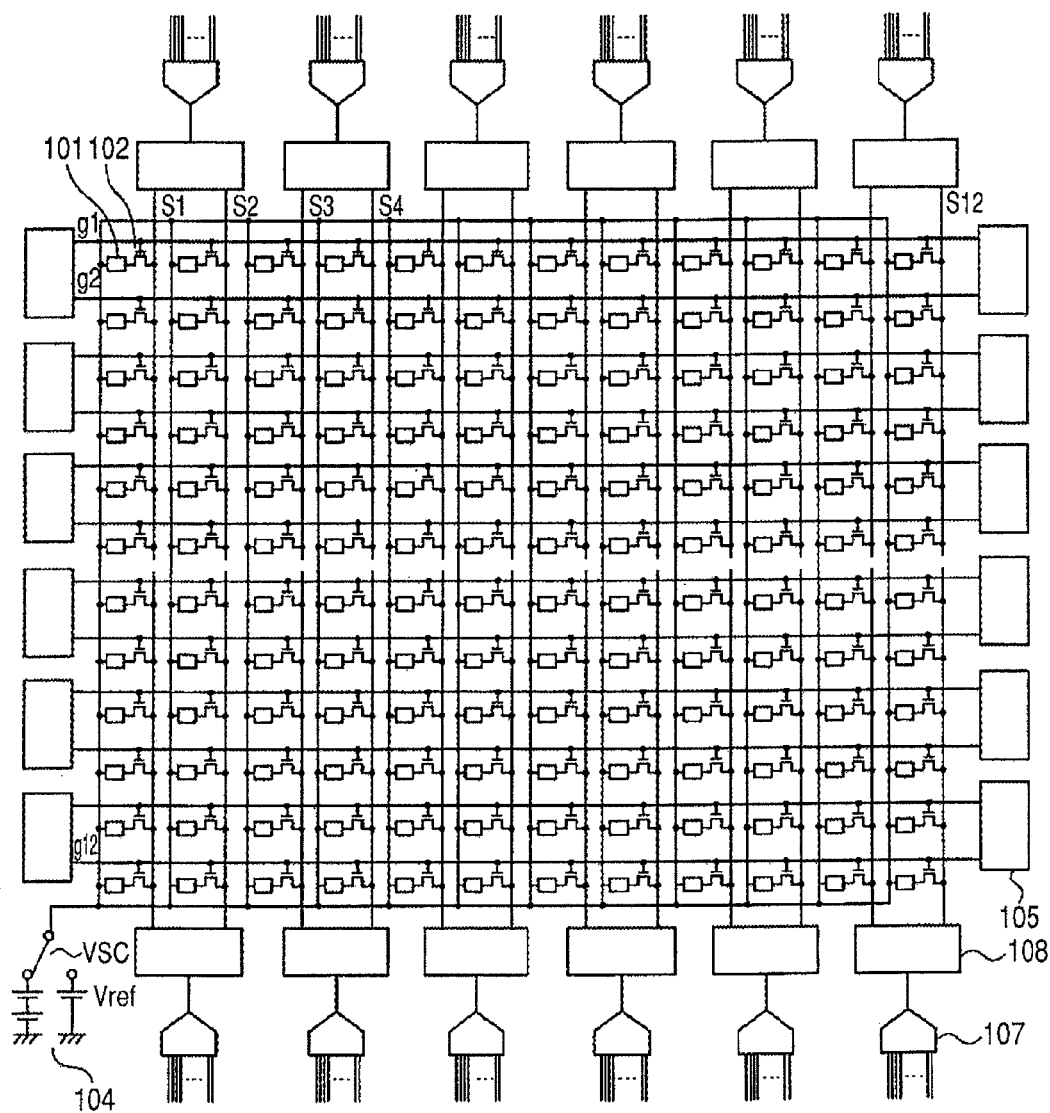
FIG. 2 is a schematic circuit diagram of the FPD using a two-dimensional area sensor with 12×12 pixels used in the radiation imaging apparatus according to the present invention.

FIG. 2 is a schematic circuit diagram of the FPD used in the radiation imaging apparatus of the present invention and using the two-dimensional area sensor with 12×12 pixels. The same constituent elements as in FIG. 1 are denoted by the same reference numerals respectively and description thereof is omitted.

In FIG. 2, a plurality of the drive circuits 105 is arranged on the two opposing sides of the two-dimensional area sensor 103 and supplies a drive signal to one drive wiring Vg1 from both opposing sides at substantially the same timing. A plurality of the read out circuits 108 is arranged on the two opposing sides of the two-dimensional area sensor 103 and reads out image signals in the divided area (sub matrix) of the two-dimensional area sensor 103 from the signal wirings commonly connected to a plurality of pixels divided among a plurality of pixels in one column, for example, to the pixels in the upper half of the two-dimensional area sensor 103.

Figure 3:
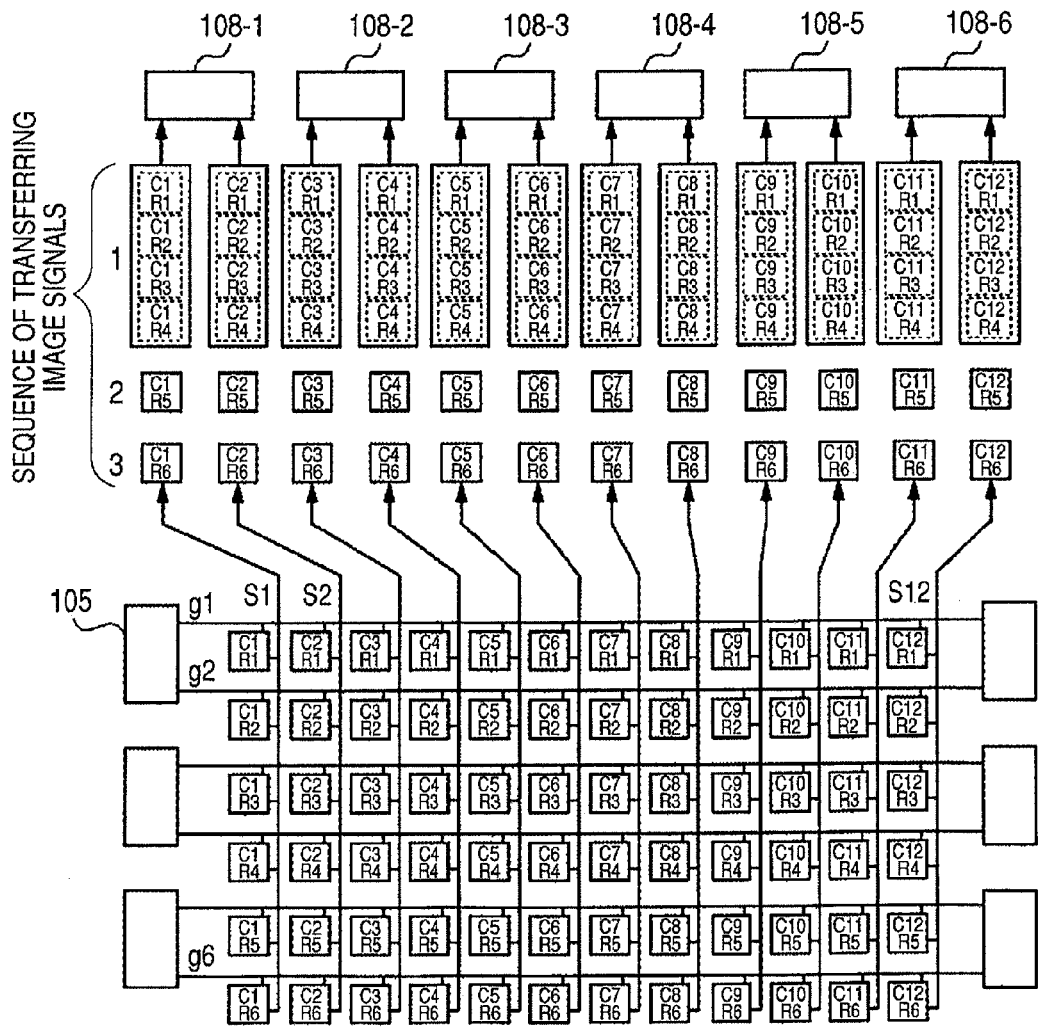
FIG. 3 is a schematic diagram describing a method of reading out images in the radiation imaging apparatus according to the present invention.

FIG. 3 is a schematic diagram describing a method of reading out images in the radiation imaging apparatus according to the present invention and describing the FPD illustrated in FIG. 2 as an example. Where, the number of pixels of 12×12 is set, for the sake of convenience, to describe the present invention. The number of pixels in the present invention does not depend on the above. The actual number of pixels in the two-dimensional area sensor used in a 17-inch radiation imaging apparatus is about 2800×2800 to 2200×2200, which depends on the size of one pixel though. The number of pixels in the two-dimensional area sensor used in a 9-inch radiation imaging apparatus is about 1400×1400 to 1100×1100.

As illustrated in FIG. 3, in the present invention, the pixels in the fifth and the sixth row being a target portion (or a predetermined area) drawing the attention of a doctor or operator are sequentially read out on a row basis. The pixels in the first to the fourth row being an area except the target portion are simultaneously read out on a plural row basis to perform the pixel addition. In this case, simultaneously reading out the pixels in the fourth row on a plural row basis and sequentially reading out the pixels in the fifth row are temporally continuously performed in a read out period of one frame. In other words, the spatially continuous pixels in and outside the predetermined area are controlled to be temporally continuously read out in one frame period.

In FIG. 3, firstly, the drive circuit 105 applies drive signals substantially at the same time to the drive wirings in the first to the fourth row to turn on the TFTs in the first to the fourth row to read out signals from the pixels in the first to the fourth row substantially at the same time to add a plurality of the pixels in the first row (C1R1 to C12R1) through a plurality of the pixels in the fourth row (C1R4 to C12R4). The signals read out substantially at the same time are read out by the read out circuits 108 as the signals of the pixels (C1R1 to C1R4), (C2R1 to C2R4), ..., (C12R1 to C12R4) on a column basis respectively. After the pixel-addition read out in the first to the fourth row has been finished, the drive signal is applied to the drive wiring in the fifth row to turn on the TFTs in the fifth row to read out signals from a plurality of the pixels in the fifth row (C1R5 to C12R5). The signals read out substantially at the same time from a plurality of the pixels in the fifth row are read out by the read out circuits 108 as the signals of the pixels (C1R5), (C2R5), ..., (C12R5) on a column basis respectively. After the pixels in the fifth row have been finished to be read out, the drive signal is applied to the drive wiring in the sixth row to turn on the TFTs in the sixth row to read out signals from a plurality of the pixels in the sixth row (C1R6 to C12R6). The signals read out substantially at the same time from a plurality of the pixels in the sixth row are read out by the read out circuits 108 as the signals of the pixels (C1R6), (C2R6), ..., (C12R6) on a column basis respectively. Performing the above operation in one frame period enables capturing image signals formed of the image signals in the target portion (or the predetermined area) with a high resolution and the pixel-addition image signals outside the predetermined area as an image for one frame, whose target portion is high in resolution. In addition, the one frame period in this case is shorter than the one frame period when all pixels are sequentially read out. Moreover, images can be obtained whose target portion (predetermined area) is higher in resolution than the images read out with all pixels added in two rows, for example.

Figure 4:
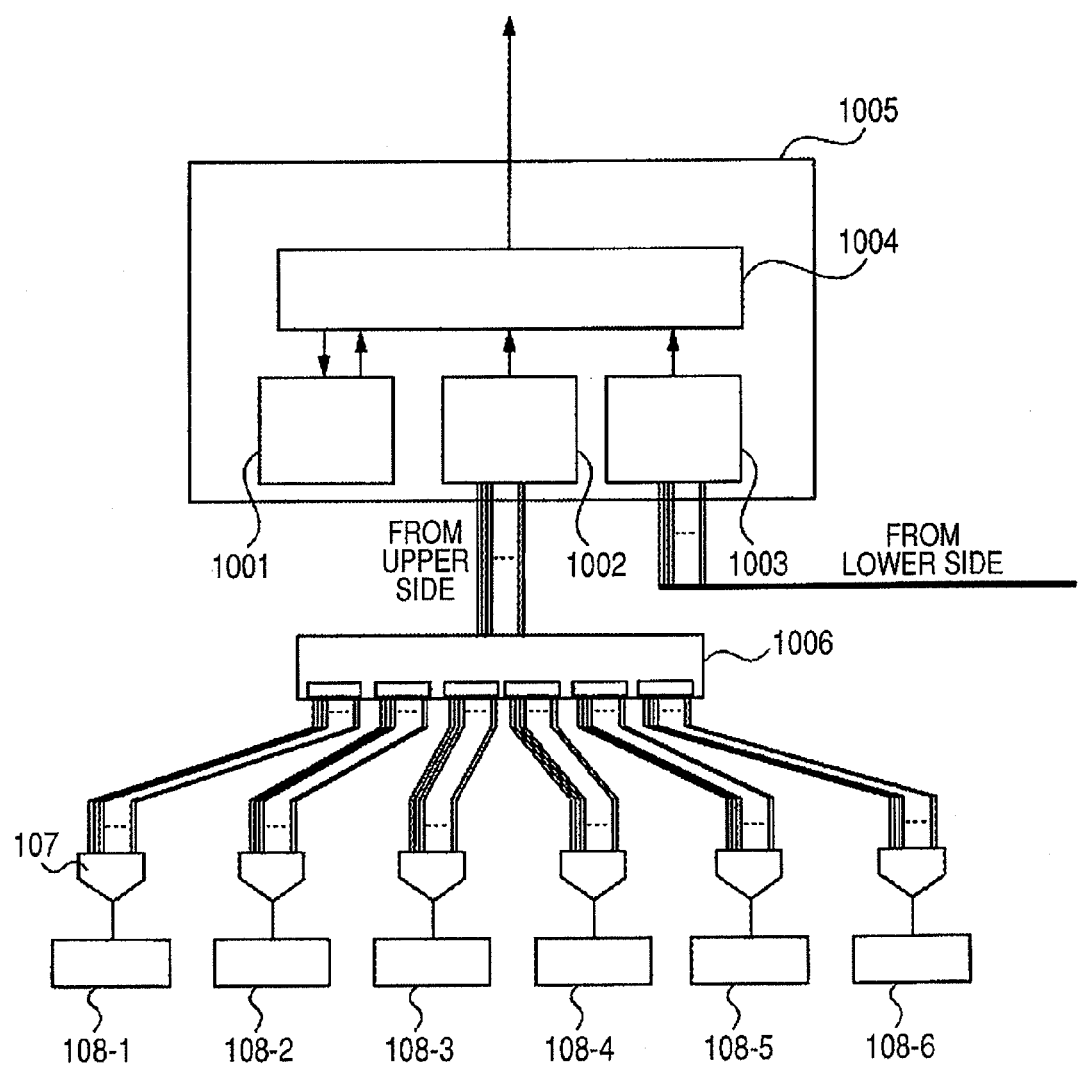
FIG. 4 is a block diagram of a data processing unit used in the radiation imaging apparatus according to the present invention.

FIG. 4 is a schematic diagram describing a method of reading out images in the radiation imaging apparatus according to the present invention and a block diagram of a data processing unit for processing digital image data transferred from the read out circuit 108 illustrated in FIG. 3 and converted by the A/D converter 107.

In FIG. 4, the data processing unit includes a digital multiplexer 1006 which transfers parallel digital signals from a plurality of A/D converters 107 as serial signals. Memories 1002 and 1003 store the serial digital signals from the digital multiplexer 1006 as image information. The memory 1002 stores, for example, digital data of the upper half of the two-dimensional area sensor and the memory 1003 stores digital data of the lower half of the two-dimensional area sensor. A computing unit 1004 computes digital data received from the memories 1002 and 1003 to be formed into image data. An image memory 1001 stores image data computed by the computing unit 1004. An image processing unit 1005 includes these 1001 to 1004 and may further include correcting data. In that case, the computing unit 1004 can perform process for correcting image data.

Figure 5:
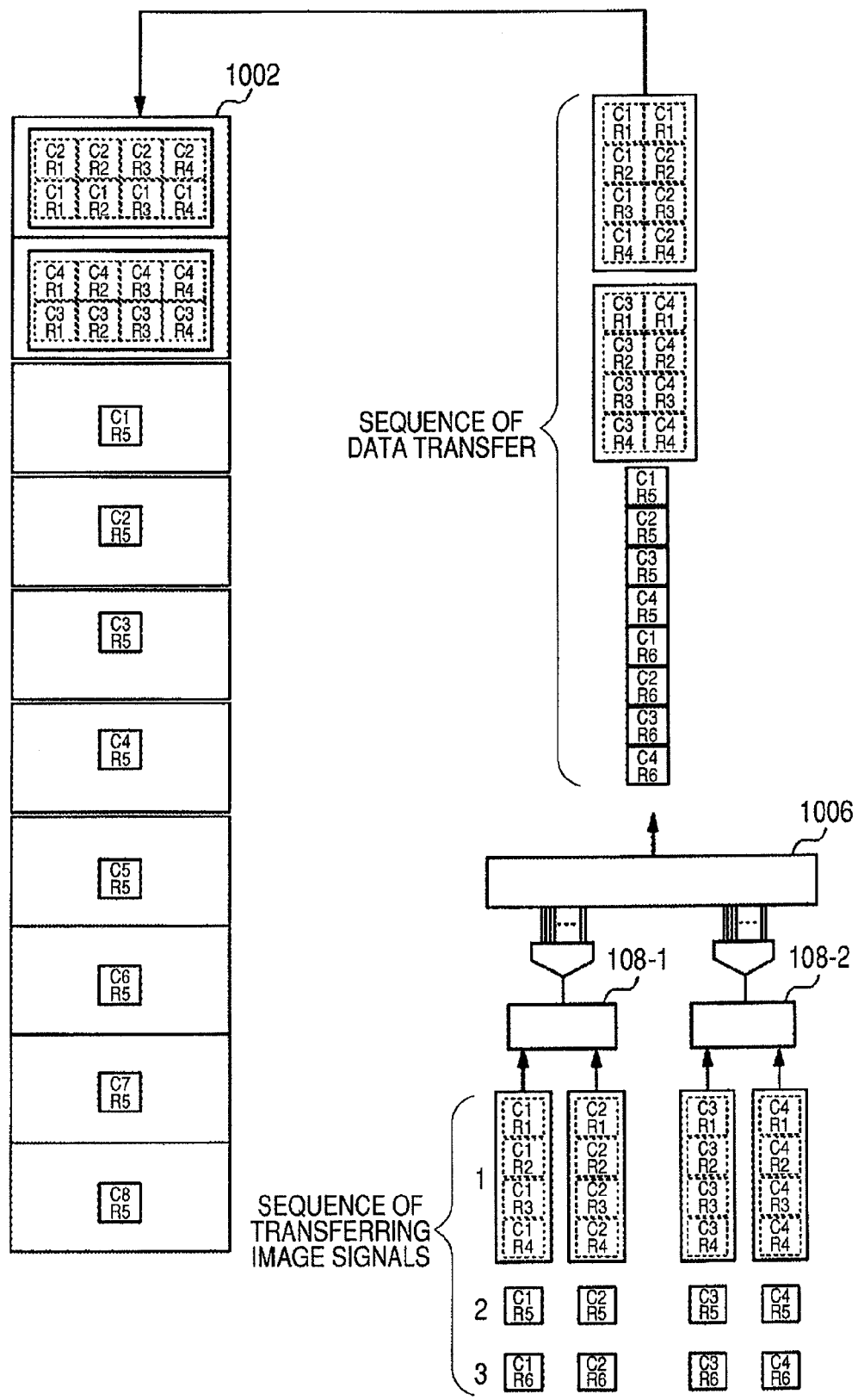
FIG. 5 is a schematic diagram describing a method of reading out images in the radiation imaging apparatus according to the present invention.

FIG. 5 is a schematic diagram describing a method of reading out images in the radiation imaging apparatus according to the present invention and describing the FPD illustrated in FIG. 3 as an example. In FIG. 5, although a description is made on transfer and storage of data from two read out circuits 108-1 and 108-2, this is set for the sake of convenience to describe the present invention. The number of read out circuits in the present invention does not depend on the above.

Firstly, the signals of the pixels in the first to the fourth row which are subjected to pixel addition and read out are read out by the read out circuit 108-1 on a column basis as signals (C1R1 to C1R4) and (C2R1 to C2R4) and by the read out circuit 108-2 as signals (C3R1 to C3R4) and (C4R1 to C4R4). The read out circuit 108-1 subjects the signals of four rows on a column basis to analog pixel addition for two columns in the column direction to output the signals of (C1R1 to C2R4) for four rows and two columns as one image signal. The read out circuit 108-2 subjects the signals to analog pixel addition for two columns in the column direction to output the signals of (C3R1 to C4R4) for four rows and two columns as one image signal. The output signals for four rows and two columns are converted into digital signals by the A/D converter 107, thereafter, converted into serial data by the digital multiplexer 1006 and stored in the memory 1002. The signals of the pixels output through the pixel addition are finally averaged to flat difference in output and resolution with the signals of the pixels read out line by line, and stored in the memory 1002 as each pixel value.

In the next place, the signals of the pixels in the fifth row are read out by the read out circuit 108-1 on a column basis as (C1R5) and (C2R5) and by the read out circuit 108-2 as (C3R5) and (C4R5). The read out signals are converted into digital signals by the A/D converter 107, thereafter, converted into serial data by the digital multiplexer 1006 and stored in the memory 1002.

The signals of the pixels in the sixth row are read out by the read out circuit 108-1 on a column basis as (C1R6) and (C2R6) and by the read out circuit 108-2 as (C3R6) and (C4R6). The read out signals are converted into digital signals by the A/D converter 107, thereafter, converted into serial data by the digital multiplexer 1006 and stored in the memory 1002.

That is to say, for the signals in the rows subjected to pixel addition for four rows as in the present embodiment, an addition average value of signals corresponding to 4×2 pixels in the two-dimensional area sensor is caused to correspond to image information of 4×4 pixels. For the signals in the rows in which pixels are read out pixel by pixel, a signal corresponding to one pixel in the two-dimensional area sensor is caused to correspond to image information of one pixel. Thus, images are processed not to be broken down.

Image signals whose part is subjected to pixel addition in a plural rows do not need to be transferred on a line basis of a signal wiring (column by column). Pixel addition is performed in the read out circuit 108 to collectively transfer signals, thereby enabling reduction in the time required for data transfer.

Figure 6:
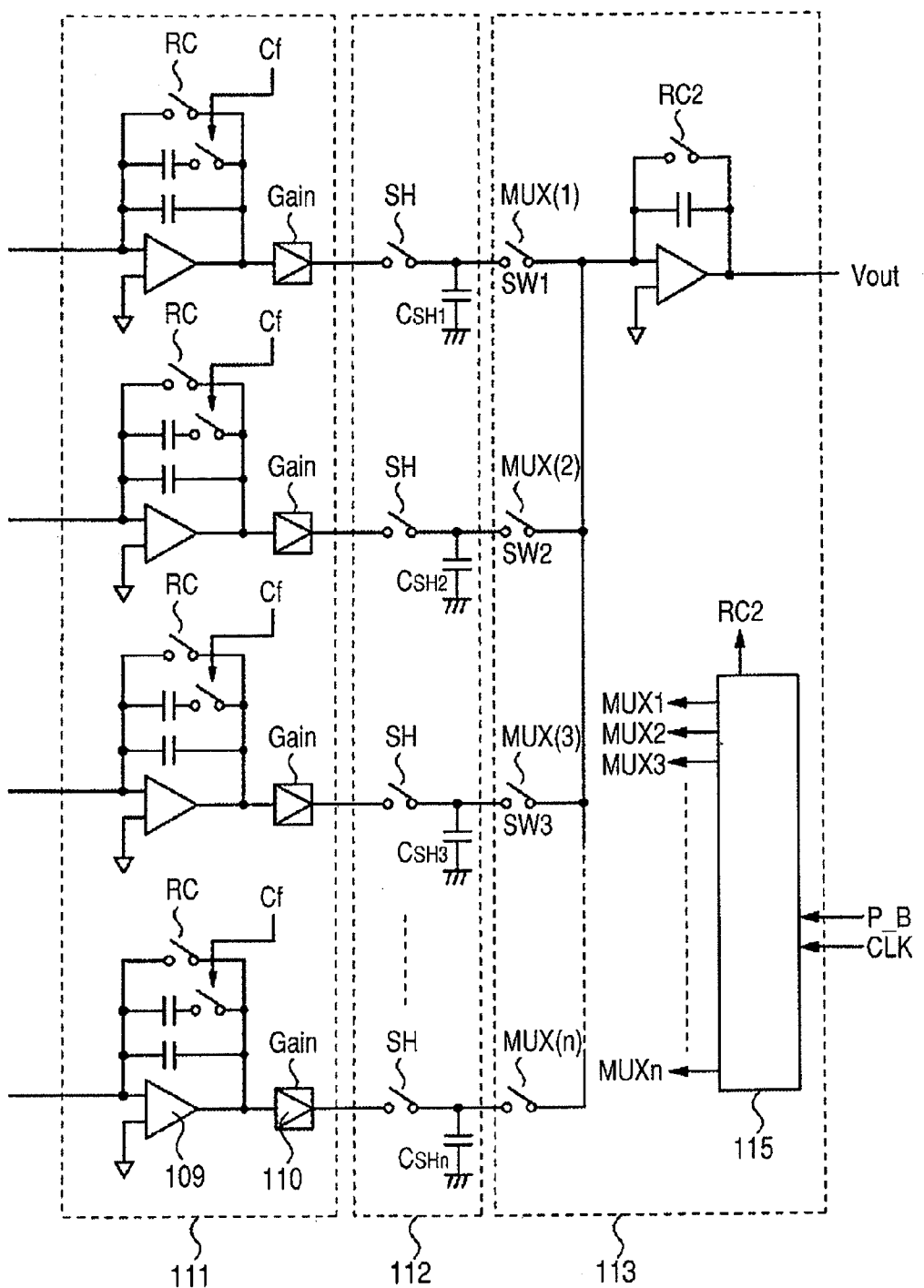
FIG. 6 is a block diagram of a read out circuit used in the radiation imaging apparatus according to the present invention.

Analog pixel-addition in the column direction in the read out circuit 108 is described referring to FIG. 6. FIG. 6 illustrates a block diagram of the read out circuit 108. The same constituent elements as in FIG. 1 are denoted by the same reference numerals and characters respectively and description thereof is omitted.

A register circuit 115 serves to supply an analog multiplexer 113 with the control signal MUX 1 to MUX 200 to control it. A method of outputting the control signals MUX is determined by a control signal P_B for controlling the number of pixels to be added to be input into the register circuit 115 and a basic clock CLK for operating the register circuit 115. When the control signal P_B is in a High state, the control signals MUX(n) and MUX(n+1) will be in a High state at the same time to perform two pixel-additions, and signals for two signal wirings are sent to the buffer amplifier 106 to add pixels. These control signals are supplied to the read out circuits from a control circuit (not shown).

The image information formed of signals converted into digital data by the above method is stored in the memory 1002. The digital signal input into the memory 1002 is sequentially written into the top address of the memory, that is, the digital signals of (C1R1 to C2R4) are written into the top address, and then (C3R1 to C4R4), (C1R5 to C2R5), . . . , (C4R6) are sequentially written and the top half of digital image data is stored in the memory 1002.

The lower half is processed in the same manner as the upper half. The lower half of digital image data is stored in the memory 1003.

Figure 7A:
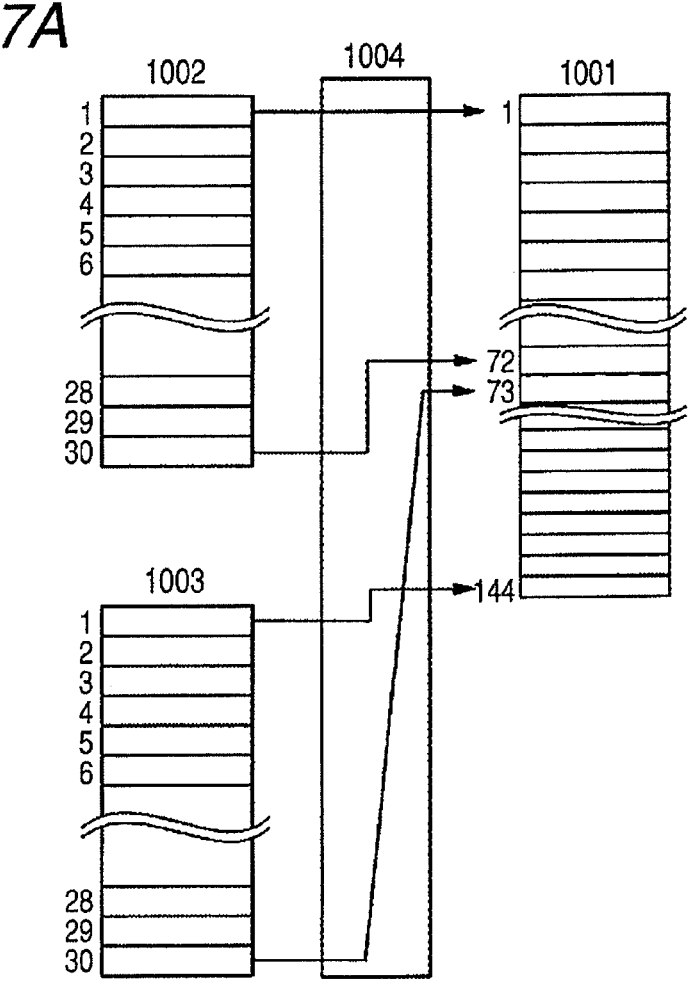
FIGS. 7A and 7B are schematic diagrams describing a method of reading images in the radiation imaging apparatus according to the present invention.
Figure 7B:
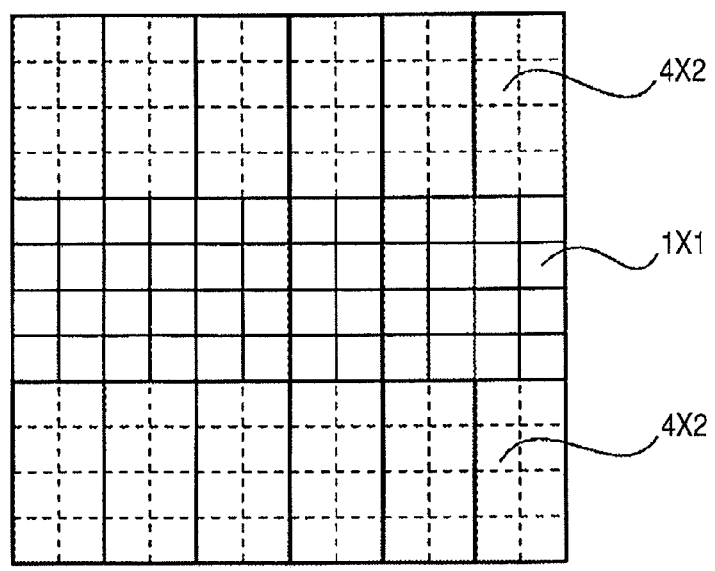

The digital image data stored in the memories 1002 and 1003 is processed as one image by the computing unit 1004 not to be broken and then stored in the image memory 1001 as illustrated in FIG. 7A. The images in the fifth to the sixth row being the target portion in the digital image data stored in the image memory 1001 is higher in resolution than the images in the first to the fourth row being non-target portion as illustrated in FIG. 7B. Thus, the image signal composed of the image signal of the target portion (predetermined area) being high in resolution and the image signal subject to pixel addition outside the predetermined area can be obtained as a one-frame image whose target portion is high in resolution.

The image data stored in the image memory 1001 is output by the image processing unit 1005, then the contrast, gradation, luminance and size thereof are processed by an external image processing apparatus (not shown) so that the image can be suited for use in surgical operation and diagnosis and the image is displayed on a display apparatus (not shown).

The ratio of the number of the read out circuits to the number of the A/D converters does not need to be one to one. The A/D converter may be connected to a plurality of the read out circuits if the A/D converter to be used is faster in drive speed than the read out circuit. In that case, an analog multiplexer is inserted between the A/D converter and the read out circuit to switch the signal of the read out circuit.

Figure 8:
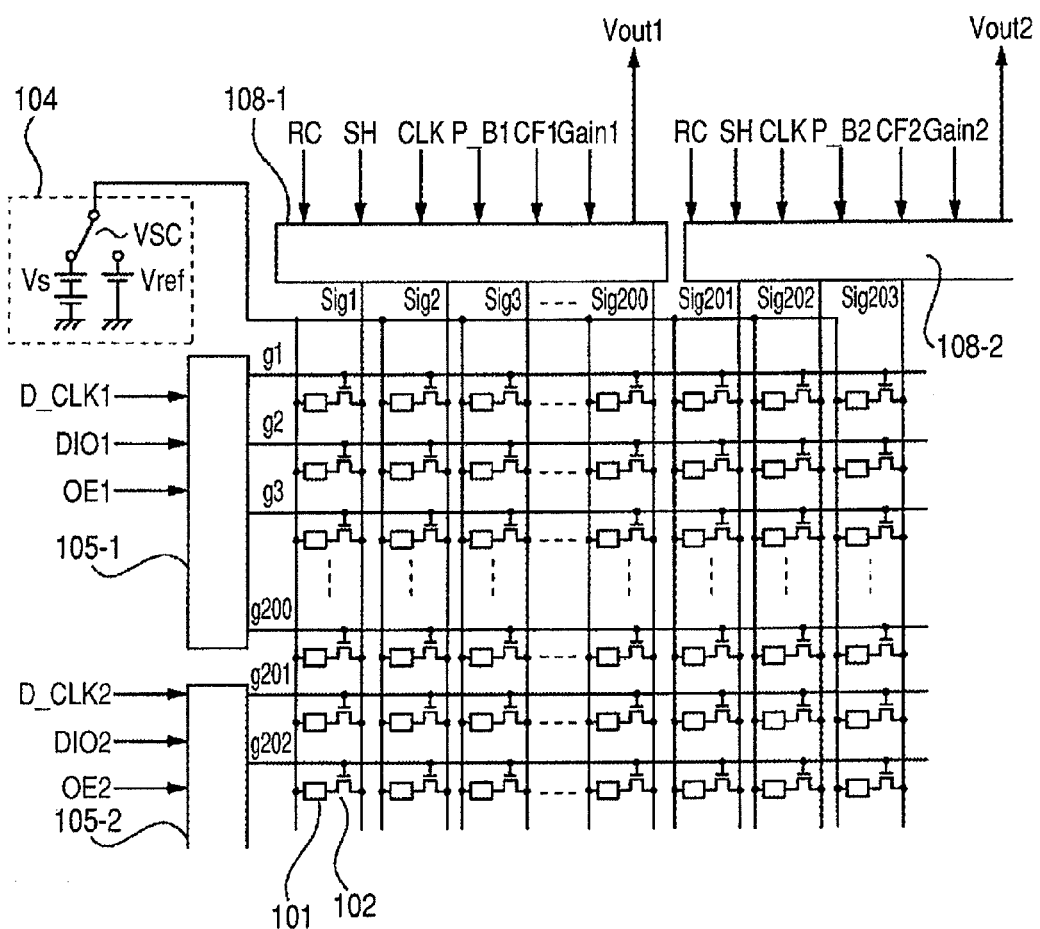
FIG. 8 is a schematic circuit diagram of the FPD used in the radiation imaging apparatus according to the present invention.
Figure 9A:
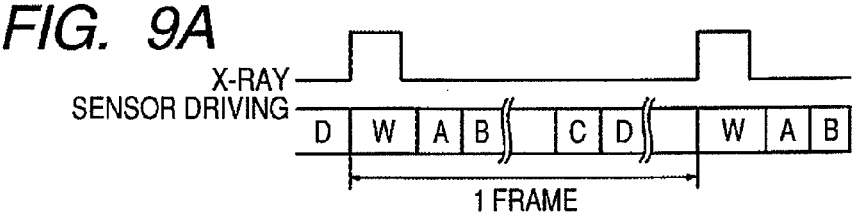
FIGS. 9A, 9B and 9C are timing charts illustrating one-frame reading out operation of the FPD used in the radiation imaging apparatus according to the present invention.
Figure 9B:
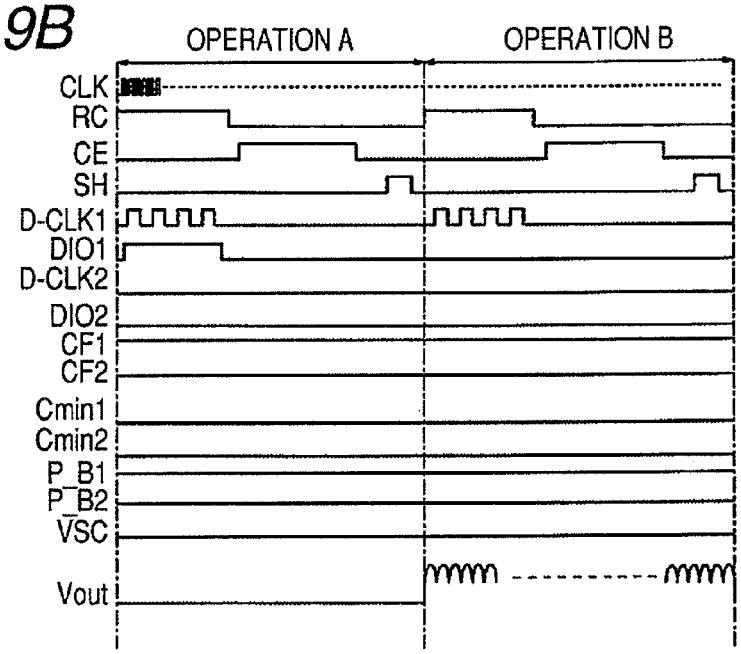
Figure 9C:
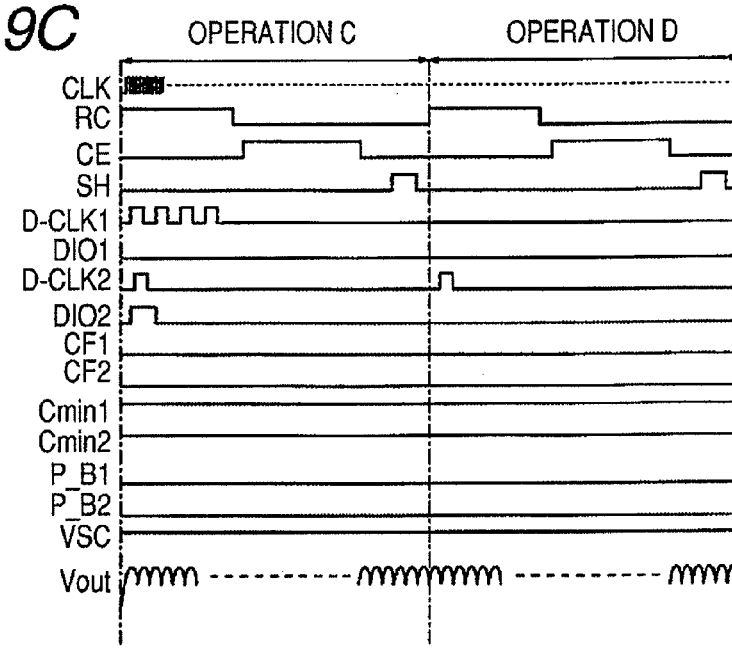

The following is a description of the read-out operation of one frame in the FPD according to the radiation imaging apparatus of the present invention with reference to FIG. 8 and FIGS. 9A, 9B and 9C. FIG. 8 is a schematic circuit diagram of the FPD according to the radiation imaging apparatus of the present invention. FIGS. 9A, 9B and 9C are timing charts illustrating the read-out operation of one frame in the FPD according to the radiation imaging apparatus. The constituent elements described above are denoted by the same reference characters as those in the above figures and description thereof is omitted.

As illustrated in FIG. 9A, the radiation imaging apparatus using the FPD captures images in such a manner that X rays being radiation are radiated during the period of operation W and light from phosphor converting the wavelength of X rays transmitted through an object is converted into an electric signal by a photoelectric conversion element and stored.

In the operation W, all TFTs are turned off and a voltage required for photoelectric conversion is applied to the photoelectric conversion element.

After the operation W has been finished, operations A, B, C and D are conducted to read out signals stored in the photoelectric conversion element. The operations A and B are conducted to add_pixels in four rows and in two columns respectively. The operations C and D are conducted to read out pixels on a row and a column basis. In the present embodiment, the pixel addition in four rows and the read out on a row basis are switched depending on whether pixels are in the target portion during the read out of one frame. The target portion starts the 201-th row.

The timing charts of the control signals in operations A to D are illustrated in FIGS. 9B and 9C. In the operation A, RC is caused to be in a High state for a certain period to reset the amplifier. Four pulses are input into D-CLK1 during the period to perform the pixel addition in four rows with DIO1 in a High state. Next, when the control signal OE is caused to be in a High state, the drive wirings g1 to g4 illustrated in FIG. 8 are simultaneously turned on to add the signals in four rows (or signals for four pixels on a single signal wiring) and transfer them to the read out circuits 108-1 and 108-2 through the signal wirings. The control signal OE is caused to be in a Low state and then SH is caused to be in a High state to perform sampling and holding. After the operation A has been finished, the operation B is conducted. The operation B is different from the operation A only in the signal of DIO1, but same in timing. The operation B is repeated for four rows. At this point, the control signals P_B1 and P_B2 are caused to be in a High state to perform the pixel addition in the column direction in the read out circuits 108-1 and 108-2. The operation B causes the read out circuits to output image signals.

After the operation B has been finished, the operation C is conducted. The operation C reads out signals row by row. In that case, one pulse of D-CLK2 is input with the DIO2 pulse in a High state, and in the operation D following the operation C, one pulse of D-CLK2 is input every time one row is read out.

The reason pulses are input into D-CLK1 in the operation C is that D-CLK signals left in the read out circuits are discharged therefrom.

After the operation C for a single row has been conducted, the operation D is conducted for the rest of the rows. At this point, the control signals P_B1 and P_B2 are caused to be in a Low state because the pixel addition in the column direction is not performed in the read out circuits 108-1 and 108-2.

The above operation allows all signals to be read out from the FPD.

In the present embodiment, although the pixels in the target portion are read out pixel by pixel by a sequential drive on a row basis and the pixels in the non-target portion are read out by a simultaneous drive on a plural row basis to add a plurality of pixels, the present invention is not limited to the above. The image in the target portion may be higher in resolution than that in the non-target portion. For example, if the number of pixels in the target portion simultaneously read out is taken to be N (where N is a natural number satisfying N≧1) and if the number of pixels in the non-target portion simultaneously read out is taken to be M (where, M is a natural number satisfying M≧2), M may be greater than N. However, since a high resolution is required in the target portion, it is more desirable to sequentially drive pixels row by row to read out pixel by pixel.

Second Embodiment

Figure 10:
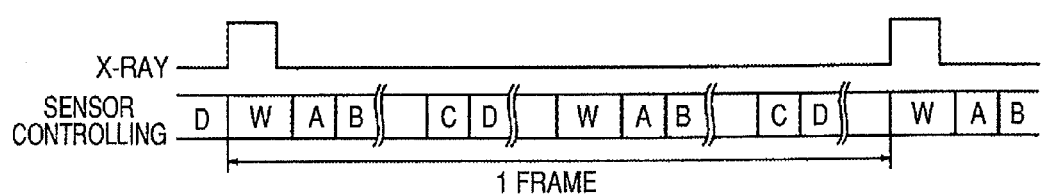
FIG. 10 is a schematic flow chart illustrating image capturing operation of the radiation imaging apparatus according to a second embodiment of the present invention.

The second embodiment related to the radiation imaging apparatus of the present invention is described using FIG. 10. FIG. 10 is a schematic flow chart illustrating the image capturing operation of the radiation imaging apparatus using the FPD in the present embodiment.

In the present embodiment, a read out operation is conducted twice every time X-rays are radiated, as is not the case with the first embodiment. The first read out operation of the two is such that X rays are radiated to read out the electric signals from the FPD based on X rays transmitted through the object. The second is to read out dark current and image lag components stored in the conversion element. Although a frame rate in this drive is lower than that in the drive described in the first embodiment, picture quality can be improved because image lag and dark current components can be removed in real time.

Third Embodiment

The following is a description of a radiation imaging system using the radiation imaging apparatus with the FPD according to the present invention with reference to the drawings.

Figure 11A:
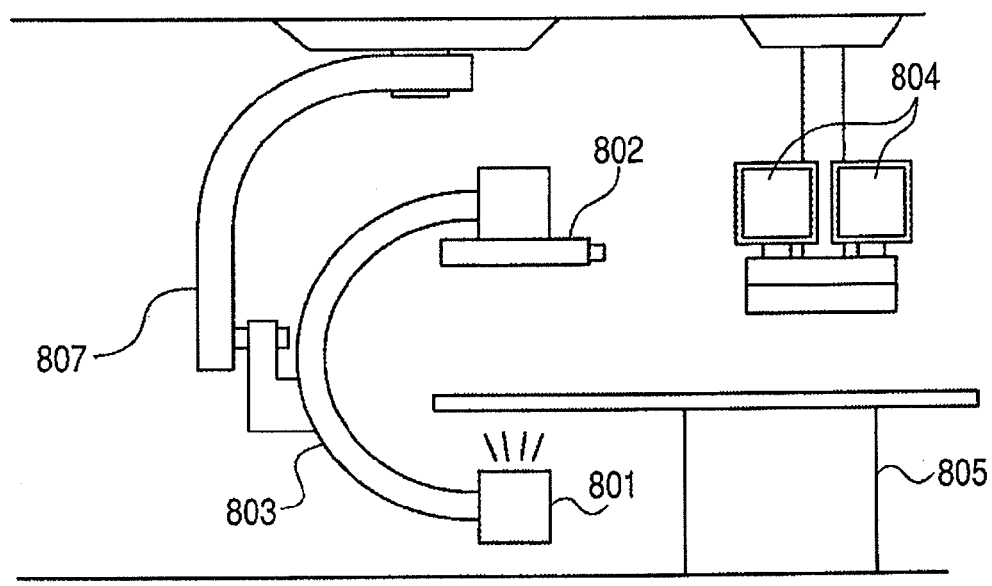
FIGS. 11A and 11B are schematic diagrams describing a radiation imaging system using the radiation imaging apparatus according to the present invention.
Figure 11B:
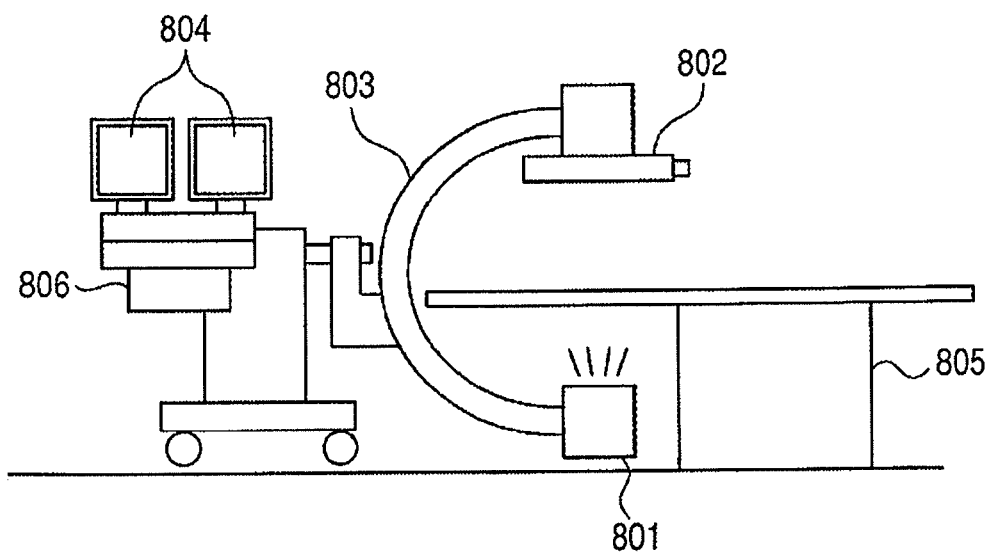

FIGS. 11A and 11B are schematic diagrams describing a fluoroscopic system using the radiation imaging apparatus with the FPD according to the present invention.

FIG. 11A is a schematic diagram of a stationary radiation imaging apparatus fixed to the ceiling of a consulting room. FIG. 11B is a schematic diagram of a mobile radiation imaging apparatus. In FIGS. 11A and 11B, the radiation imaging system includes a radiation generating unit 801 for generating radiation such as X rays, flat panel detector (FPD) 802, holding unit 803 referred to as C-type arm for holding the radiation generating unit 801 and the flat panel detector 802, display unit 804 capable of displaying radiographic image information captured by the flat panel detector 802, bed 805 for placing thereon an object, carriage 806 capable of carrying the radiation generating unit 801, flat panel detector 802, holding unit 803 and/or display unit 804 and of controlling these units and mounting unit 807 for mounting the radiation generating unit 801, flat panel detector 802 and holding unit 803.

Figure 12A:
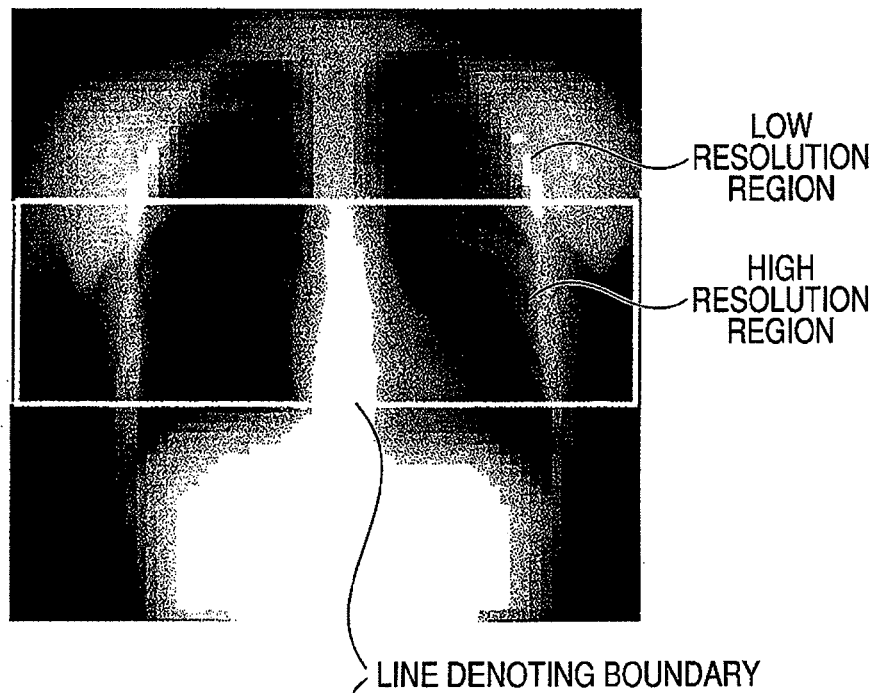
FIGS. 12A and 12B are radiation images captured by the radiation imaging apparatus according to the present invention.
Figure 12B:
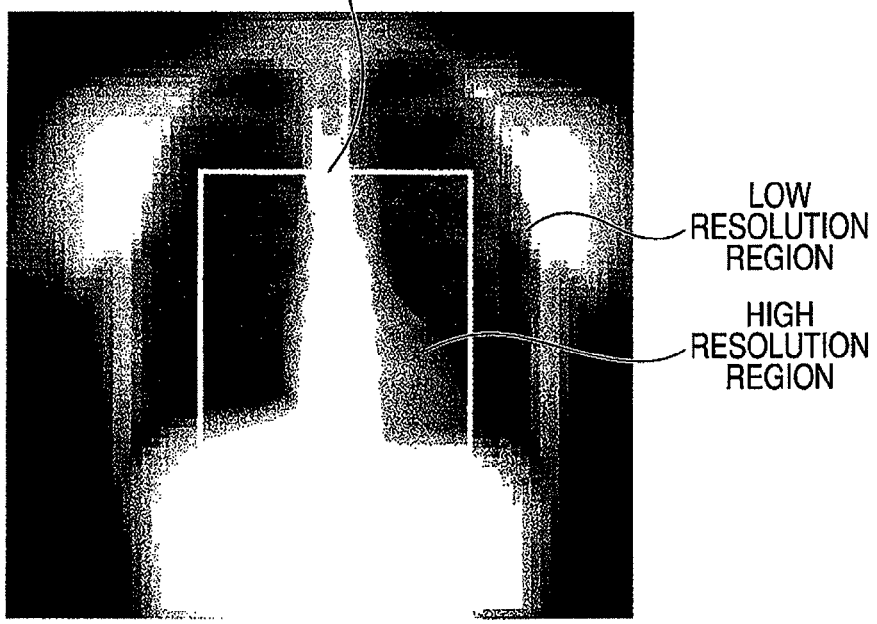

FIGS. 12A and 12B schematically illustrate images displayed on the display unit 804 when the fluoroscopic image of the chest is radiographed using the present invention.

FIG. 12A is a radiation image obtained by the drive described in the first embodiment. FIG. 12B is a radiation image which is driven and processed so that a high resolution portion can be formed into a square shape. In order to obtain the image in FIG. 12B, the pixel addition is performed in the read out circuits except for the center area in the drive described in the first embodiment, or the pixel addition and average are performed in the read out circuits for the central area in the horizontal direction in the image processing.

When images are displayed on the display unit 804, a line may be displayed on a border between the images which are subjected to the pixel addition, read out and is lower in resolution and the images which are not subjected to the pixel addition, read out and is higher in resolution to discriminate them. The line is desirably displayed on the side where resolution is lower on the border. This display allows an operator to readily discriminate the border between the high and the low resolution, improving workability. A high resolution area may be designated by a control console or a touch panel monitor. A designated area is intermittent because the number of pixels to be added can be switched only on a vertical drive circuit basis described above, however, the area is determined to be close to the area where the operator designates.

It should also be understood that the foregoing embodiments are merely examples of the embodiment to carry out the present invention, and the technical scope of the present invention should not be construed in a restrictive manner by those embodiments. That is, in the present invention, various modifications could be made without departing from the spirit or essential features of the invention.

In addition, the embodiment of the present invention can be realized by causing, for example, a computer to execute a program. Means for supplying a program to a computer, such as, for example, recording medium which can be read out by a computer such as CD-ROM in which the program is stored or transmission medium such as the Internet for transmitting the program may be applied as the embodiment of the present invention. Furthermore, the above program can be applied as the embodiment of the present invention. The above program, recording medium, transmission medium and program product fall within the scope of the present invention.

The present invention relates to a radiation imaging apparatus suitably used for medical diagnosis and is used in particular in a radiation imaging apparatus including a flat panel detector (FPD) formed of semiconductors as a detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-213470, filed Aug. 4, 2007, which is hereby incorporated by reference herein in its entirety.

What is claimed is:

1. An imaging apparatus comprising:
an area sensor in which a plurality of pixels are arranged in a matrix, the pixels including conversion elements for converting incident radiation or light into electric charge;
a drive circuit unit for supplying a drive signal to a plurality of drive wirings arranged in a column direction, wherein each of the drive wirings is connected commonly to a plurality of pixels arranged in a row direction;
a read out circuit unit for reading out signals from the pixels through a plurality of signal wirings arranged in the row direction, wherein each of the signal wirings is connected commonly to the plurality of pixels arranged in the column direction; and
a processing unit processing signals transferred from the read out circuit unit, wherein
N is an integer of one or more,
M is an integer of two or more and always greater than N,
the drive circuit unit and the read out circuit unit perform a first operation in which signals are simultaneously read out from N pixels in a first area of the area sensor and a second operation in which signals are simultaneously read out from M pixels in a second area except the first area of the area sensor,
the first and the second read out operations are continuously performed in a period while signals for one frame are read out from pixels of the area sensor, and
a first signal obtained by the first read out operation and a second signal obtained by the second read out operation are continuously transferred from the read out circuit unit to the processing unit.

2. The imaging apparatus according to claim 1, wherein the first read out operation is continuously performed after the second read out operation in the period, and the first signal is continuously transferred from the read out circuit unit to the processing unit after the second signal.

3. The imaging apparatus according to claim 1, wherein the drive circuit unit simultaneously supplies a drive signal to the N drive wirings in the first area at the first read out operation and simultaneously supplies the drive signal to the M drive wirings in the second area at the second read out operation.

4. The imaging apparatus according to claim 1, wherein the read out circuit unit reads out a signal from the N signal wirings in the first area at the first read out operation and reads out a signal from to the M signal wirings in the second area at the second read out operation.

5. The imaging apparatus according to claim 1, wherein the processing unit generates an image signal for one image using the first and the second signal.

6. The imaging apparatus according to claim 1, comprising a control unit for controlling the drive circuit unit and/or the read out circuit unit, wherein the control unit supplies a first control signal causing the drive circuit unit and/or the read out circuit unit to perform the first read out operation and a second control signal causing the drive circuit unit and/or the read out circuit unit to perform the second read out operation to the drive circuit unit and/or the read out circuit unit.

7. The imaging apparatus according to claim 6, wherein the drive circuit unit comprises a plurality of drive circuits and the control unit supplies the first control signal to the drive circuits connected to the drive wirings in the first area and the second control signal to the drive circuits connected to the drive wirings in the second area.

8. The imaging apparatus according to claim 7, wherein the read out circuit unit comprises a plurality of read out circuits and the control unit supplies the first control signal to the read out circuits connected to the signal wirings in the first area and the second control signal to the read out circuits connected to the signal wirings in the second area.

9. The imaging apparatus according to claim 1, wherein the conversion element includes a wavelength converter convening incident radiation into light and a photoelectric conversion element convening light from the wavelength converter into electric charge.

10. The imaging apparatus according to claim 1, wherein the drive circuit unit and the read out circuit unit continuously perform the first and the second read out operation during two consecutive radiations out of plural radiations of the radiation or light and after the period when signals are read out from all pixels in the area sensor.

11. A method of driving an imaging apparatus, wherein the imaging apparatus comprises:
an area sensor in which a plurality of pixels are arranged in a matrix, the pixels including conversion elements for converting incident radiation or light into electric charge;
a drive circuit unit for supplying a drive signal to a plurality of drive wirings arranged in a column direction, wherein each of the drive wirings is connected commonly to a plurality of pixels arranged in a row direction;
a read out circuit unit for reading out signals from the pixels through a plurality of signal wirings arranged in the row direction, wherein each of the signal wirings is connected commonly to the plurality of pixels arranged in the column direction; and
a processing unit processing signals transferred from the read out circuit unit, wherein
N is an integer of one or more,
M is an integer of two or more and always greater than N,
the drive circuit unit and the read out circuit unit perform a first operation in which signals are simultaneously read out from N pixels in a first area of the area sensor and a second operation in which signals are simultaneously read out from M pixels in a second area except the first area of the area sensor,
the first and the second read out operations are continuously performed in a period while signals for one frame are read out from pixels of the area sensor, and
a first signal obtained by the first read out operation and a second signal obtained by the second read out operation are continuously transferred from the read out circuit unit to the processing unit.

* * * * *